United States Patent [19]

Gerry et al.

[11] Patent Number: 4,654,254
[45] Date of Patent: Mar. 31, 1987

[54] ADHESIVE TAPE

[75] Inventors: Elisabeth H. Gerry, Wellesley Hills, Mass.; Timothy L. Sergeant, Seneca, S.C.

[73] Assignee: The Kendall Company, Boston, Mass.

[21] Appl. No.: 659,589

[22] Filed: Oct. 11, 1984

[51] Int. Cl.⁴ ............................................. C09J 7/02
[52] U.S. Cl. .................................. 428/252; 428/259; 428/343; 428/354
[58] Field of Search ............... 428/229, 259, 248, 252, 428/343

[56] References Cited

U.S. PATENT DOCUMENTS

| | | | |
|---|---|---|---|
| 3,400,004 | 9/1968 | Corry | 428/259 |
| 3,853,598 | 12/1974 | Ragase | 428/261 X |
| 4,303,724 | 12/1981 | Sergeant et al. | 428/229 |
| 4,439,482 | 3/1984 | Suematsu | 428/259 X |

Primary Examiner—Thomas J. Herbert
Attorney, Agent, or Firm—Francis J. Clark

[57] ABSTRACT

An adhesive tape or the like is described comprising cotton warp yarns and textured polyester filler yarns having a layer of pressure sensitive adhesive disposed thereon. This invention includes the use of heavy denier textured polyester filler yarns because these yarns have the ability to spread out upon the application of pressure thereby filling the fabrics interstices thus preventing the adhesive that has been deposited on this backing fabric from penetrating through the fabric. The construction of the adhesive tape disclosed herein improve qualities such as the tear characteristics; flexibility; conformability; and blocking of the tape, while providing a tape that may be manufactured economically.

2 Claims, 4 Drawing Figures

ADHESIVE TAPE

BACKGROUND OF INVENTION

This invention relates to an adhesive tape and more particularly it describes a medical athletic adhesive tape. Some such prior art tape fabrics and backing materials have been constructed of spun warp yarns and a high number of spun filler yarns coated on one side with a primer and having an adhesive disposed thereon. Still other (U.S. Pat. No. 4,303,724) have been made from spun warp yarns and a low number of textured filler yarns having a plastic film backing attached thereto and an adhesive disposed thereon.

The aforementioned prior art athletic tape constructions were developed to give properties such as improved tear and adherence to the back surface of a tape when one layer of tape is crossed over another layer during an application.

Generally, an athletic tape should have properties such as: flexibility, conformability, and a significant reduction in blocking. For the purposes of this application, flexibility, conformability, and blocking are defined as follows: Flexability is demonstrated when a tape has excellent stretch capabilities in the crosswise direction which enable the tape to distort before wrinkling. Conformability is a tape, due to its stretchability, easily conforms to the various contours of the human body to which it is applied. Blocking is the adherence of material, such as tape, to itself and is referred to when material is wound upon itself, as is done in winding a roll of tape.

The aforementioned properties are essential qualities in an athletic adhesive tape and will be further discussed in subsequent paragraphs.

Some prior art attempts include U.S. Pat. No. 3,853,598 which discloses an adhesive tape composed of a closely woven high thread count synthetic fiber backing, coated on one side with a primer which bonds the fibers of the fabric together. Applied to the primer side of the fabric is an adhesive mass which is used to adhere the tape to the skin of the human body. It is stated in the patent that the adhesive mass does not enter into the synthetic fiber backing but only directly contacts the primer. Also, the fabric may be torn in either direction, and the fabric is said to provide excellent adherence to the back surface of a tape when one layer of tape crosses over a previously applied layer during an application.

There are several disadvantages associated with this prior art fabric. One disadvantage is that the fabric is a closely woven high thread count fabric. When a fabric has a high thread count and is closely woven, stiffness is inherently built into the fabric in the weaving process, thus making the fabric harsh, less flexible and less apt to conform to body members. As mentioned in an earlier paragraph, flexibility, and conformability are necessary requirements for a medical or athletic tape fabric. Users of such adhesive tape require a tape to be soft, flexible, and conformable so that when it is applied to a human body it will not be harsh against the skin and will follow the contours of any body member without wrinkling. Another disadvantage of this fabric is that it uses a primer as a base for the adhesive mass. To apply a primer to a fabric requires an additional step in the manufacturing process thus making this fabric more costly to manufacture than the present invention. One other disadvantage of this prior art fabric pertains to the adherence of one layer of tape to the other when they are crossed over each other. If the tape adheres to itself when crossed over itself in an application then it will adhere to itself when it is wound upon itself as when wound in a roll. The adherence or blocking of the tape to itself in a roll makes it very difficult to unwind and, therefore, is a constant irritation to personnel using the tape.

U.S. Pat. No. 4,303,724, of common assignee, discloses an adhesive duct tape for wrapping heating ducts comprising a layer of polyolefin film as a backing sheet with a reinforcing fabric containing textured yarn and having an adhesive disposed thereon. This patent is primarily concerned with the tear characteristics of the fabric but makes reference to some reduction in the amount of adhesive that has to be used on the fabric. The patent states that the textured yarns in the fabric allow said fabric to be torn in a smooth and even manner with a minimum amount of force being used.

A distinct disadvantage to this fabric is that it requires the use of a polyolefin film attached to the back surface of the fabric. By using a polyolefin film as a backing sheet in conjunction with the other components of the fabric, stiffness becomes inherently, and advantageously from this products viewpoint built into the fabric. The polyolefin backing film by itself may be considered pliable but once the composite of woven material, adhesive and plastic film are assembled together then the structure takes on different properties, such as stiffness. Stiffness, as discussed in an earlier paragraph, is an undesirable quality and unacceptable to persons who use tape. Another disadvantage related to the use of a backing film sheet is that the use of said film makes it necessary to have an additional step in the manufacturing process to laminate the film to the fabric thus adding to the cost of the fabric.

Thus, the prior art has made many attempts to provide an adhesive tape that would have properties such as flexibility, conformability, and essentially no blocking for wrapping peoples limbs, but has been unsuccessful in providing such a tape. Accordingly, the present invention utilizes less components than the prior art but provides an adhesive tape that is soft, flexible, and has conformability. The present invention also unexpectedly provided two additional benefits not found in the prior art. First, the degree of widthwise give of the fabric, or more specifically, the fabrics widthwise elongation was substantially improved. Second, a substantial reduction of blocking is achieved resulting in a tape that when rolled or wound onto itself and then unwound, does not adhere to itself.

SUMMARY

This invention relates to an adhesive tape comprised of cotton warp yarns and textured polyester filler yarns having a layer of adhesive disposed thereon. This invention is particularly well suited for use as an athletic adhesive tape. The use of textured polyester filler yarns having a denier of between 40 to 200 reduces the number of filler yarns per inch of fabric required in such a fabric because the textured yarns spread out in the woven fabric and fill the spaces between the warp and filler yarns thus permitting such a tape to have excellent flexibility and conformability. In addition to filling the spaces in the fabric, the textured yarn also prevents the adhesive, which is applied to the surface of the yarns, from penetrating through the fabric thereby inhibiting the blocking properties of this tape.

An object of this invention is to provide an adhesive tape that is more flexible than prior art adhesive tapes.

Another object of this invention is to provide an adhesive tape that has conformability.

Still another object of this invention is to provide an adhesive tape that has good unwind characteristics which may also be referred to as a reduction in blocking.

An additional object of this invention is to provide an adhesive tape that has widthwise elongation.

Yet another object of the present invention is to provide all the above advantages and improved characteristics while keeping the cost of manufacturing such a tape to a minimum.

DESCRIPTION OF THE PREFERRED EMBODIMENT

Figure 1:
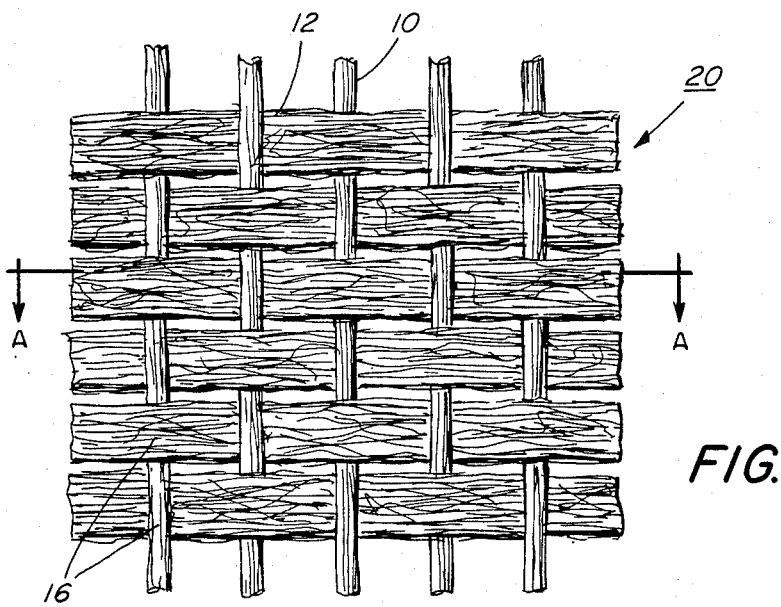
FIG. 1 is a bottom view of an adhesive tape which allows the cotton warp yarns and the textured filler yarns to be shown to illustrate the textured yarn filling the spaces between the yarns.
Figure 4:
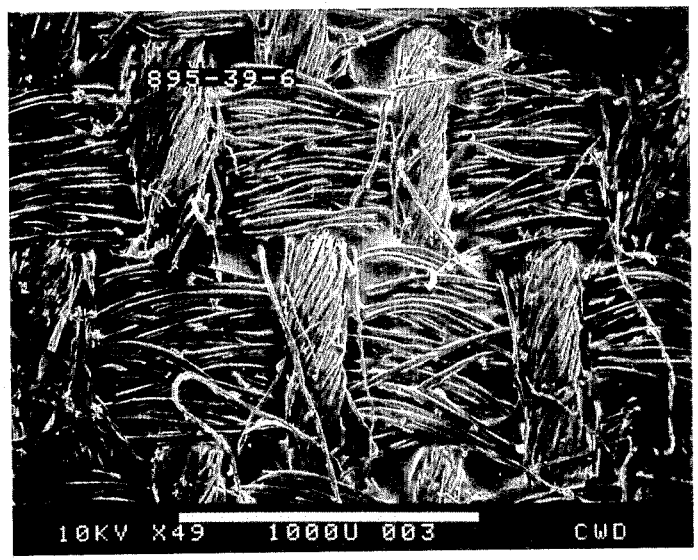
FIG. 4 is a photomicrograph of the present invention to further illustrate its unique structure.

Although the preferred application of the present invention is for use as an athletic tape, it is also well suited for use as hospital and surgical tape. Referring to the drawings, FIG. 1 is a bottom view of an adhesive tape 20 which shows the cotton warp yarns 10, the textured polyester filler yarns 12 and the bottom side 16 of the tape 20 without an adhesive. It should be noted that cotton for the warp yarn and textured polyester for the filler yarn are only the preferred yarns. The warp yarns may be other natural yarns or even a combination of natural and synthetic yarns and the filler yarns may be other synthetic textured yarns taken from the class comprising polyester, polyamide and polyolefin fibers. The use of other than the preferred yarns may give similar but some what less desireable results. FIGS. 1 and 4 also illustrate that the textured polyester filler yarn spreads out with the application of pressure, thereby substantially eliminating the spaces between the warp and filler yarns. This is important because when an adhesive mass, preferably a pressure sensitive adhesive, is applied to a surface of a woven fabric, the textured yarn, due to its ability to spread out and fill the fabrics interstices, prevents the adhesive mass from penetrating through the fabric thus allowing the bottom side 16 of the tape 20 to remain substantially free of any adhesive, as is shown in FIG. 4. The textured polyester filler yarn should advantageously range in size between 40 to 200 denier. It was determined after making samples of tape fabrics that the denier of the textured yarn in the preferred embodiment should be at approximately 150 denier because this size yarn spreads out in the fabric sufficiently to fill the spaces in the fabric.

Still, another important consideration in manufacturing this tape is the yarn count. The weave in the present invention may range between 40 to 80 warp yarns and 20 to 58 filler yarns, although the preferred weave is 63 warp yarns and 40 filler yarns (63/40). It was discovered during experiments that the preferred weave of 63 warp yarns and 40 filler yarns of 150 denier optimumly prevented the adhesive from penetrating through the fabric but still provided sufficient conformability as to advantageously be used to wrap body limbs, or the like.

Figure 2:
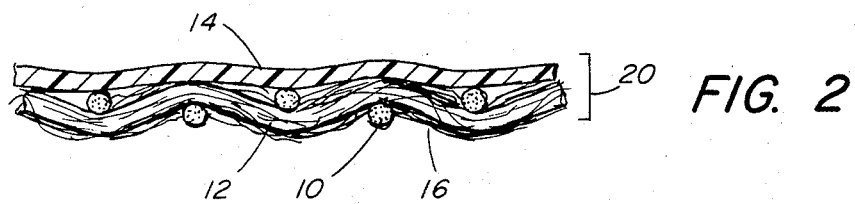
FIG. 2 is a cross-sectional view A-A' of FIG. 1 illustrating the warp yarns, filler yarns, and the adhesive mass disposed thereon.

Other combinations of warp and filler yarns within the above range may be used to accomplish similar results but the quality of the results may not be same. The preferred embodiment as illustrated in FIG. 2 shows the adhesive mass 14 disposed on the fabric of cotton warp yarn 10 and polyester textured filler yarn 12. The present invention by having cotton warp yarns maintains the tear property of the tape and also remains similar to an all cotton tape. Tear properties are important because they allow the user to easily tear off a section of tape without difficulty. Tear properties are important in several types of tape, for example, athletic tape, medical and surgical tape, and industrial tape such as automotive and electrical tapes. FIG. 2 further illustrates that the bottom side 16 of the tape 20 is substantially free of adhesive. This is important because if adhesive were allowed to bleed through or penetrate the fabric, each surface of the tape would have adhesive on it and the surfaces would tend to adhere to themselves when wound onto themselves as in a roll. But when penetration of an adhesive through a fabric is controlled as is done in the present invention and no adhesive bleeds or penetrates through to the bottom side of the fabric, good unwind characteristics are achieved and blocking of the tape 20 to itself is virtually eliminated. Unwind characteristics may be defined, for the purpose of this application, as the ability of a surface with adhesive thereon to release itself from another non-adhesive surface with a minimum amount of force being used.

Good unwind characteristics are required in an adhesive tape, because when a fabric or tape has an adhesive disposed on one side thereof and the tape is then wound onto itself, as in a roll, you do not want the tape to adhere or block to itself. As already noted herein, adherence of tape to itself is commonly referred to as blocking. Blocking may make it extremely difficult or totally impossible to unwind tape which has been wound into rolls. This difficulty in unwinding of rolls of tape has created a continuous source of irritation to the people using the tape and render it essentially useless. With the advent of the present invention, a substantial advance in the art has been made by virtually eliminating blocking problems of prior conformable wrapping tapes. Referring again to FIGS. 1 and 4 which illustrate the 63/40 weave showing that the fabric has essentially no open spaces between the warp 10 and filler yarns 12. This is not only important because it prevents the adhesive from penetrating through the fabric as previously mentioned but it is also important because when the adhesive side of the tape is wound or crossed over the back surface or non-adhesive side, as when a tape is being used in an application, only very slight adherence if any at all, to the surfaces may take place. This advantageous property is due to the 63/40 weave and the high denier textured polyester yarn used in the present invention because this weave and yarn, after spreading, results in a conformable, porous surface essentially of fibers and not a solid or stiff surface that is prevalent in prior art. This fibrous surface, therefore, results in a reduced surface area. This invention with a reduced surface area will allow only a discontinuous contact with any adhesive surface that may come in contact with it. Discontinuous contact with a surface for the purpose of this application is defined as an intermittent point contact.

Figure 3:
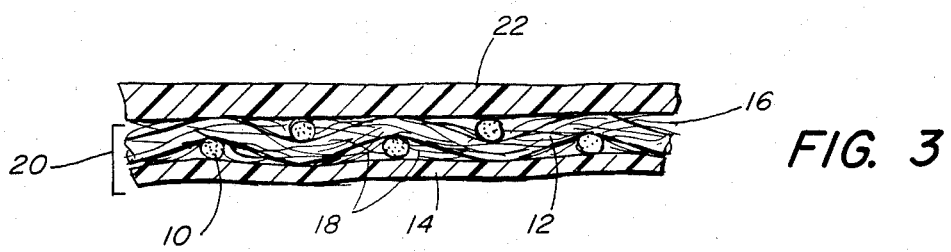
FIG. 3 is a segment taken from FIG. 2 to show the fibers on the bottom side in contact with an adhesive surface.

This discontinuous contact is due to the fact that only fibers on the surface of this invention will make point contact with the adhesive, therefore, they will not adhere very well to the surface. This point contact with the surface fibers also enhances the unwind characteristics mentioned earlier because with discontinuous contact, only a minimum amount of force would be needed to break any contact between an adhesive and a non-adhesive surface. This is illustrated in FIG. 3, a segment of FIG. 2, wherein fibers 18 of the textured polyester filler yarn 12 are shown on the bottom side 16 of tape 20 after spreading of the yarn 12. The fibers 18 of the tape 20 are shown in contact with an adhesive surface 22 to illustrate this discontinuous point contact. This reduction in surface area is not present in the prior art, because prior art tapes uses plastic films or other continuous smooth substrates on the back surface of a tape thereby exposing a larger surface area for the adhesive to adhere to. It should be noted that although the prior art uses a continuous backing sheet, there is no backing sheet used in the present invention. Because the present invention does not use a backing sheet and the fact that fewer textured yarns per inch of fabric have to be employed in the present invention the fabric is extremely flexible and, therefore, results in a product with excellent conformability. This flexibility comes about because, as mentioned previously, the present invention fabric with a smaller number of textured yarns which have the ability to spread out within the fabric, results in the fabric having a high degree of mobility. Therefore, the fabric of this invention has a special advantage over the prior art when it is utilized in pressure sensitive tapes or other adhesive-coated assemblies that are designed for wrapping around contoured or angled surfaces. In particular, the special characteristics of this fabric are advantageous when the adhesive-coated fabric must be made to conform to body surfaces such as fingers, ankles, wrists, and the like.

The aforementioned benefits of using textured yarns as the filler yarn derive from the greater extensibility of such yarns when compared to conventional yarns and particularly when compared to cellulosic yarns, commonly used in industry in the prior art backing fabrics employed for similar applications. It is known to textile technologists that fabric distortion decreases with the increase in crimp of the crossing thread or yarn. Textured yarns confer the behavior characteristics of highly crimped yarns thus less buckling or distortion occurs with increase in crimp or extensibility of the filler yarn. Expressed in another way, when a fabric is under deformation that leads to stress, resistance to creasing and wrinkling is enhanced by use of more resilient yarns. The backing fabric of this invention is distinctly orthotropic, that is, the material possesses two definite axes of symmetry in one important mechanical property, that is, extensibility. These two axes lie perpendicular to each other. This behavior is illustrated by elongation to break testing of the fabric. Thus, the elongation to rupture in the machine direction, or where the warp yarns are in tension, is less than 5% whereas the elongation to break in the cross machine direction, or where the filling yarns are in tension, is over 25%. In contrast the prior art fabrics commonly and previously used, for example, a 70×42 all cotton fabric, has a breaking elongation of less than 5% in both machine and cross machine directions.

The ability to parallelogram or prevent jamming of yarns and consequent wrinkling or distortion of the fabric is further indicated in that the fabric of this invention exhibits an elongation to break of over 25% when stretched at an angle of 45 degrees from the machine direction. The construction described herein, where highly extensible textured filler yarns replace the relatively inextensible cellulosic or non-textured yarns of prior art, leads to a lower shear modulus of the fabric when stress is exerted at an angle to the machine direction. Since the textured yarns shear more easily, the fabric shows less tendency to buckle and wrinkle when stress is applied at angles or directions other than zero (machine direction) or 90 degrees (cross direction). As a consequence of the orthotropic geometry of this invention, greater conformity to rounded contours and a greater resistance to wrinkling is exhibited when pulled in a direction other than the machine direction during wrapping. By the use of textured filler yarn in the fabric, elongation in a widthwise direction is achieved. This elongation is due to the ability of the textured yarn to stretch and recover is determined in the process of making textured yarns wherein a false twist, which is an actual twisting of the yarn, is mechanically introduced into the yarn after which the yarn is untwisted. Although the twist is removed from the yarn, it retains a memory of the twist, thus remaining stretchable. Due to this widthwise elongation, the fabric may distort before wrinkling thus enhancing the flexibility and conformability of the fabric. Flexibility in the fabric tape allows the tape to move at different angles, angles that are needed when wrapping or winding a tape around part of the body, such as ankles or knees. Conformity in the present invention allows the tape when being applied to parts of the body to contour to the body. If the tape does not flex or conform when applied to parts of the body, it will be uncomfortable and irritable to the person to whom it has been applied.

Prior art could not provide this flexibility or conformability because either a high count or yarns per inch of the fabric was used or a plastic backing sheet was used in conjunction with the fabric and neither of these are conducive to providing flexibility or conformability as was discussed in earlier paragraphs. Adhesive tapes need to be flexible and have conformity in order to meet the demands of people who use athletic tape or the like.

The following are examples of the preferred embodiment and are not intended to limit the present invention to other than the claims that follow:

EXAMPLE 1

To make an athletic tape, a fabric consisting of 30/1 cotton warp yarns and 150/32 texturized polyester filler yarns, with a thread count of 63×40, was calendered to apply a tackified rubber based pressure-sensitive adhesive to one side thereof. The adhesive composition was 33% pale crepe, 25% tackifiers, 23% zinc oxide, 7% clay filler, 5% titanium dioxide to give a white color, 4% processing oil, with the remaining ingredients being crosslinking agents and antioxidants. A standard calender technique was used, with temperatures at 230° F. top roll, 190° F. center roll and 190° F. bottom roll. The line speed was 40 yards a minute. Three mils of mass were on the center roll of the calender and, the cloth was 7.0 mils thick. The overall thickness of the tape was 7.5 mils indicating that the adhesive was deeply anchored to the back cloth. Even with the rather heavy coverage, no strike through of the adhesive to the other side of the fabric was noted. In addition, because of the coverage, no release treatment of the cloth was required. After adhesive coating, the tape was slit and wound onto cores to make rolls of tape.

EXAMPLE 2

To make a medical tape, a fabric consisting of cotton warp yarns and 70 denier texturized polyester filler yarns was coated with an acrylic pressure-sensitive adhesive by reverse roll application on a spread line. The acrylic adhesive was polymerized in an emulsion using the monomers 2—ethylhexyl acrylate, methyl acrylate, ethyl acrylate, acrylic acid, and styrene. The latex was then thickened by addition of 1% poly-acrylate thickener and raising the ph to 8.5. The tape was then dried with oven zone temperatures at 200° F., 250° F., and 275° F., giving an adhesive thickness of 1.5 mils over the backing. Because of the excellent coverage of this cloth construction, there was no strike through of the adhesive to the other side of the fabric during coating and no release treatment was required. The tape was then slit and wound onto cores or spools for hypo-allergenic hospital tape.

What is claimed is:

1. An adhesive tape comprising a fabric backing consisting of warp yarns selected from the group of natural fibers, synthetic fibers, or blends thereof and textured synthetic filler yarns having between 40 and 200 denier, said fabric containing between 40 and 80 warp yarns and between 20 to 58 filler yarns and having a pressure sensitive adhesive disposed on one side thereof.

2. The adhesive tape of claim 1 wherein the yarn count is 63 warp yarns and 40 filler yarns with the filler yarns having a denier of 150.

* * * * *